United States Patent [19]

Chabardes et al.

[11] Patent Number: 4,636,570

[45] Date of Patent: Jan. 13, 1987

[54] TOCOPHEROL DERIVATIVES USEFUL IN THE SYNTHESIS OF VITAMIN E AND THEIR PREPARATION

[75] Inventors: Pierre Chabardes, Sainte Foy les Lyon; Michel Mulhauser, Charriere Blanche, both of France

[73] Assignee: Rhone-Poulenc Sante, Courbevoie, France

[21] Appl. No.: 777,846

[22] Filed: Sep. 19, 1985

[30] Foreign Application Priority Data

Sep. 20, 1984 [FR] France .................................. 84 14426
Mar. 15, 1985 [FR] France .................................. 85 03843

[51] Int. Cl.$^4$ .......................................... C07D 311/72
[52] U.S. Cl. ..................................... 549/408; 549/410; 549/411
[58] Field of Search ............................. 549/408, 410

[56] References Cited

U.S. PATENT DOCUMENTS 4,544,758  10/1985  Vogel et al. .......................... 549/410

FOREIGN PATENT DOCUMENTS 12824  7/1980  European Pat. Off. .

OTHER PUBLICATIONS

Stalla-Bourdillon, Industrie Chimique Belge, 35, pp. 13, 22-23 (1970).

Primary Examiner—Nicky Chan
Attorney, Agent, or Firm—Stevens, Davis, Miller & Mosher

[57] ABSTRACT

Tocopherol derivatives of the formula:

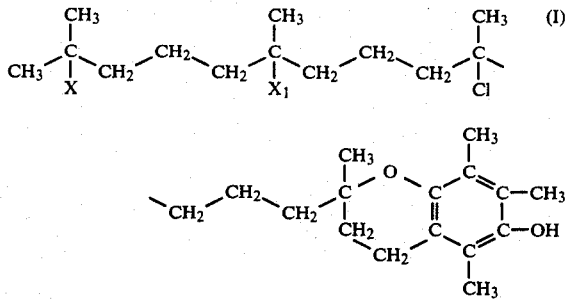

in which X and $X_1$, which may be identical or different, each represent hydrogen or chlorine and their acetates are useful in the synthesis of vitamin E.

5 Claims, No Drawings

TOCOPHEROL DERIVATIVES USEFUL IN THE SYNTHESIS OF VITAMIN E AND THEIR PREPARATION

The present invention relates to tocopherol derivatives, their preparation and their use, in particular in the synthesis of vitamin E.

The invention provides the new tocopherol derivatives of the formula:

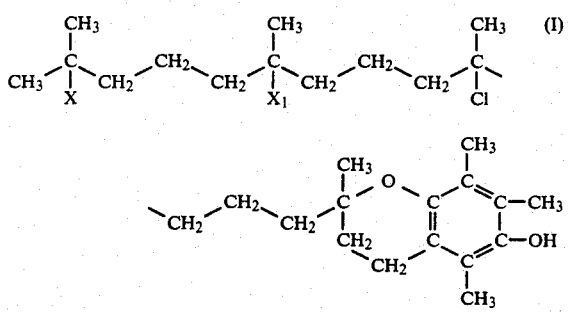

in which X and $X_1$, which may be identical or different, each represent hydrogen or chlorine.

According to a feature of the invention, the new compounds of formula (I) are obtained by condensing a compound of formula:

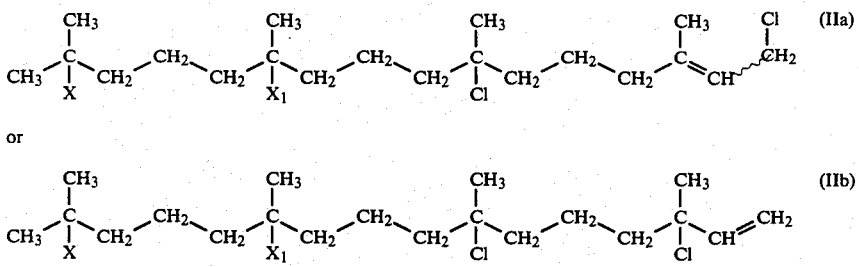

in which X and $X_1$, which may be identical or different, each represent hydrogen or chlorine or their mixtures, with trimethylhydroquinone.

The condensation is generally carried out in the presence of zinc chloride, in an organic solvent preferably chosen from among acetic acid and dioxane, at a temperature of between 0° to 50° C.

The acetate of a compound of formula (I) can be obtained by acetylation of the product of formula (I) e.g. with acetic anhydride, in the presence of zinc chloride or in the presence of a mixture of triethylamine and dimethylaminopyridine, at a temperature of about 20° C.

The compounds of formula (IIa) and (IIb) can be obtained by hydrochlorination of a polyene of the formula:

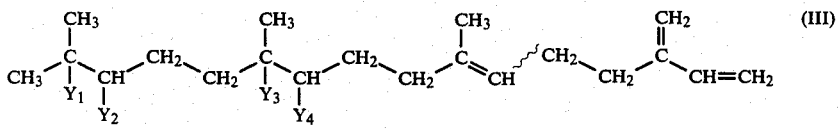

in which $Y_1$ represents hydrogen or chlorine and $Y_2$ represents hydrogen or $Y_1$ and $Y_2$ together form a valency bond, and $Y_3$ and $Y_4$ each represent a hydrogen atom or together form a valency bond, with anhydrous hydrogen chloride in the presence of a cuprous halide, such as cuprous chloride or cuprous iodide, together with a quaternary ammonium salt, such as a tetraalkylammonium halide or a trialkylamine hydrohalide, or a phosphonium salt, such as a tetraalkylphosphonium halide, in an inert organic solvent preferably chosen from the halogenated aliphatic hydrocarbons (e.g. methylene chloride), the carboxylic acids (e.g. acetic acid), the carboxylic acid anhydrides (e.g. acetic anhydride), the aliphatic hydrocarbons (e.g. hexane), the cycloaliphatic hydrocarbons (e.g. cyclohexane) or the aromatic hydrocarbons (e.g. benzene) at a temperature below 20° C. and preferably below 0° C. If the symbols Y each represent a hydrogen atom, at least two moles of anhydrous hydrogen chloride are used per mole of product of the general formula (III). If the symbols Y together form a valency bond, at least three moles of anhydrous hydrogen chloride are used per mole of product of the general formula (III).

The products of the formula (III) in which $Y_3$ and $Y_4$ each represent a hydrogen atom and $Y_1$ and $Y_2$ each represent a hydrogen atom or together form a valency bond can be prepared under the conditions described in U.S. Pat. No. 4,292,459.

The product of formula (III) in which $Y_1$ represents chlorine, $Y_2$ represents hydrogen and $Y_3$ and $Y_4$ together form a valency bond can be obtained from myrcene by condensing the magnesium derivative of 1,7-dichloro-3,7-dimethyl-octene with 3-chloro-myrcene.

1,7-Dichloro-3,7-dimethyl-octene can be obtained by reacting myrcene with at least two moles of anhydrous hydrogen chloride per mole of myrcene in the presence of a catalyst consisting of a cuprous halide, such as cuprous chloride or cuprous iodide, together with a quaternary ammonium salt such as a tetraalkylammoniun halide or trialkylamine hydrohalide, or a phosphonium salt such as a tetraalkylphosphonium halide, in an inert organic solvent chosen from halogenated aliphatic hydrocarbons (e.g. methylene chloride), the carboxylic acids (e.g. acetic acid), the carboxylic acid anhydrides (e.g. acetic anhydride), the aliphatic hydrocarbons (e.g. hexane), the cycloaliphatic hydrocarbon (e.g. cyclohexane) or the aromatic hydrocarbons (e.g. benzene), at a temperature below 20° C. and preferably below 0° C.

The magnesium derivative of 1,7-dichloro-3,7-dimethyloctene is obtained under the usual conditions by reaction of 1,7-dichloro-3,7-dimethyl-octene with magnesium in an organic solvent chosen from the ethers (e.g. diethyl ether or tetrahydrofuran) at a temperature below 0° C.

The condensation of the magnesium compound of 1,7-dichloro-3,7-dimethyl-octene with 3-chloro-myrcene is generally carried out at a temperature below 0° C. in an organic solvent chosen from the ethers (e.g. diethyl ether or tetrahydrofuran) in the presence of a cuprous halide such as cuprous iodide.

The product of the formula (III) in which $Y_1$ and $Y_2$ and and $Y_3$ and $Y_4$ respectively form a valency bond, that is to say β-springene, can be obtained by reaction of the magnesium derivative of geranyl chloride and neryl chloride with 3-chloro-myrcene.

The mixture of geranyl chloride and neryl chloride can be obtained by hydrochlorination of myrcene in the presence of one mole of anhydrous hydrogen chloride per mole of myrcene under the conditions described above for the preparation of 1,7-dichloro-3,7-dimethyl-octene.

The magnesium derivative of the mixture of geranyl chloride and neryl chloride can be obtained under the conditions described above for the preparation of the magnesium derivative of 1,7-dichloro-3,7-dimethyl-octene.

The products of the general formula (I) and their acetates, obtained by the process of the present invention, are particularly useful in the synthesis of vitamin E.

For example, the hydrogenation of a product of the general formula (I) or of its acetate, carried out with hydrogen in the presence of a catalyst such as palladium on charcoal in an organic solvent such as acetic acid or ethanol, at a temperature of between 50° and 100° C., if appropriate under pressure, gives tocopherol or tocopherol acetate.

The examples which follow show how the invention can be put into practice.

EXAMPLE 1

Trimethylhydroquinone (8.4 g), 1,7,11,15-tetrachloro-3,7,11,15-tetramethyl-hexadec-2-ene (22 g) and acetic acid (30 cc) are introduced into a 250 cc reactor. A solution of zinc chloride (1.5 g) in anhydrous acetic acid (15 cc) is then added in the course of 10 minutes. The temperature rises from 25° to 30° C. The reaction mixture is stirred for 2 hours at 30° C. and is then poured into a mixture of hexane (100 cc) and water (100 cc). The organic phase is separated by decanting and washed with a mixture (100 cc) of methanol and water (50:50 by volume). A white precipitate forms in the hexane phase, and this is filtered off and washed with a mixture (50 cc) of methanol and water (50:50 by volume). After the precipitate has been dried under reduced pressure, 2,5,7,8-tetramethyl-2-(4',8',12'-trichloro-4',8',12'-trimethyl-tridecyl)-chroman-6-ol (14.3 g) is obtained in the form of white crystals melting at 102°–104° C. The yield is 62%.

The structure of the product obtained is confirmed by the mass spectrum and the proton nuclear magnetic resonance and 13C nuclear magnetic resonance spectra.

1,7,11,15-Tetrachloro-3,7,11,15-tetramethyl-hexadec-2-ene can be prepared in accordance with one of the following processes:

(a) Triethylamine hydrochloride (3.4 g), cuprous chloride (2.5 g) and methylene chloride (270 cc) are introduced, under an argon atmosphere, into a 500 cc three-neck flask equipped with a magnetic stirrer, a thermometer and a dip tube. The mixture is cooled to −10° C. and to the homogeneous yellow solution thus obtained is added myrcene (136 g=1 mole) of purity greater than 95%, followed, over the course of 6 hours, by anhydrous hydrogen chloride (80 g). The solution thus obtained is kept at −25° C. for 18 hours.

The reaction mixture is poured into a mixture of a 10% strength aqueous ammonium chloride solution (400 cc) and pentane (300 cc). After phase separation, the organic phase is washed with water (3 times 200 cc) and then dried over potassium carbonate. After filtration and evaporation of the solvent, a pale yellow oil (237.8 g) essentially containing 1,7-dichloro-3,7-dimethyl-oct-2-ene in the form of a mixture of the E and Z isomers is obtained.

Magnesium (12.15 g), tetrahydrofuran (30 cc) and one crystal of iodine are introduced into a 250 cc reactor. The mixture is cooled to −20° C. and a solution of 1,7-dichloro-3,7-dimethyl-oct-2-ene (20.9 g) obtained above in tetrahydrofuran (85 cc) is added over the course of 5 hours 30 minutes. Stirring is continued for 18 hours at −20° C. The excess magnesium is removed by filtration and the solution is then introduced into a dropping funnel, with exclusion of air and moisture.

Copper iodide (0.5 g) and tetrahydrofuran (5 cc) are introduced into a reactor (250 cc), and some of the solution of the magnesium compound (1.5 cc) is then added. Thereafter, 3-chloro-myrcene (19.5 g), of purity greater than 87%, in tetrahydrofuran (10 cc) is added rapidly. The mixture is cooled to −20° C. and the remainder of the solution of the magnesium compound is then added over the course of 3 hours. The temperature is allowed to return to about 20° C. over the course of 1 hour. Water (5 cc) and pentane (100 cc) are added to the reaction mixture. The organic phase is separated off by decanting and dried over magnesium sulphate. After filtration and evaporation of the solvent an oil (29.7 g) is obtained.

According to vapour phase chromatographic determination with an internal standard, the degree of conversion of the 3-chloromyrcene is 69%.

The oil obtained is heated to 100°–105° C. under reduced pressure (0.5–1 mm Hg; 0.067–0.13 kPa) to remove the unreacted $C_{10}$ products.

The residue obtained (20 g) contains 85% of 15-chloro-3-methylene-7,11,15-trimethyl-hexadeca-1,6,10-triene.

The yield is 82% relative to the 3-chloro-myrcene consumed.

The structure of the product obtained is confirmed by the mass spectrum and the proton nuclear magnetic resonance spectrum.

Triethylamine hydrochloride (0.48 g), methylene chloride (15 cc), acetic acid (10 cc) and cuprous chloride (90 mg) are introduced, under an argon atmosphere, into a 250 cc reactor. The reaction mixture is stirred until a homogeneous soution is obtained. This is cooled to −10° C. and 15-chloro-3-methylene-7,11,15-trimethyl-hexadeca-1,6,10-triene (10 g) are then added followed, over the course of 1 hour, by dry hydrogen chloride gas (3.9 g). The reaction mixture is poured into an aqueous solution (100 cc) of ammonium chloride (100 g/liter). The organic phase is separated off by decanting and the aqueous phase is extracted with methylene chloride (twice 100 cc). The combined organic phases are washed with water (100 cc) and then dried over potassium carbonate. After filtration and evaporation of the solvent, 1,7,11,15-tetrachloro-3,7,11,15-tetramethyl-hexadec-2-ene (13.1 g) is obtained in a yield of 96.5%.

The structure of the product obtained is confirmed by the mass spectrum.

(b) Triethylamine hydrochloride (0.48 g), methylene chloride (15 cc), acetic acid (10 cc) and cuprous chloride (90 mg) are introduced, under an argon atmosphere, into a 250 cc reactor. The reaction mixture is stirred until a homogeneous solution is obtained. This is cooled to −10° C. and β-springene (10 g) is then added, followed over the course of 1 hour by dry hydrogen chloride gas (5.2 g). After the reaction mixture has been treated under the conditions described above, 1,7,11,15-tetrachloro-3,7,11,15-tetramethyl-hexadec-2-ene (14.2 g) is obtained in a yield of 94%.

The structure of the product obtained is confirmed by its hydrogenation to phytane.

EXAMPLE 2

Molten zinc chloride (0.22 g), trimethylhydroquinone (2.47 g) and anhydrous dioxane (10 cc) are introduced into a 250 cc reactor. The mixture is heated to 40°–45° C. and a solution of 1,7,11,15-tetrachloro-3,7,11,15-tetramethyl-hexadec-2-ene (6.8 g) in dioxane (7 cc) is then added over the course of 20 minutes. Stirring is continued for 1 hour 30 minutes. The reaction mixture is poured into an aqueous solution (50 cc) of ammonium chloride (100 g/liter). The batch is extracted with ethyl acetate (twice 50 cc) and the organic phases are then dried over magnesium sulphate. After filtration and evaporation of the solvent, 2,5,7,8-tetramethyl-2-(4′,8′,12′-trichloro-4′,8′,12′-trimethyltridecyl)-chroman-6-ol is obtained in a yield of 43.5%.

EXAMPLE 3

The product (2.1 g) obtained in Example 1, dimethylaminopyridine (150 mg) and triethylamine (10 cc) are introduced, under an argon atmosphere, into a three-neck flask and acetic anhydride (6 cc) is then added rapidly, with stirring, at a temperature of 25° C. After 1 hour's stirring, water (20 cc) is added and the reaction mixture is then neutralised by gradual addition of sodium carbonate until the evolution of carbon dioxide gas ceases. The reaction mixture is extracted with ethyl acetate (twice 50 cc). The organic phase is washed with an 0.1N aqueous hydrochloric acid solution (3 times 50 cc). The organic phases are dried over magnesium sulphate. After filtration and evaporation of the solvent, the residue obtained is taken up in hexane. The precipitate which forms is filtered off. This gives 2,5,7,8-tetramethyl-2-(4′,8′,12′-trichloro-4′,8′,12′-trimethyl-tridecyl)-chroman-6-ol acetate, melting at 95°–105° C., in a yield of 93%.

The structure of the product obtained is confirmed by the mass spectrum and the proton nuclear magnetic resonance and $^{13}C$ nuclear magnetic resonance spectra.

EXAMPLE 4

The product (5 g) obtained in Example 1, acetic acid (20 cc) and anhydrous zinc chloride (320 mg) are introduced, under an argon atmosphere, into a reactor. A solution (5 cc) of hydrochloric acid in acetic acid, containing 1.9 moles of hydrochloric acid per liter, is added. Thereafter, acetic anhydride (2.7 cc) is added over the course of 15 minutes. The temperature rises from 20° to 30° C. After 2 hours' stirring, water (10 cc), sodium acetate (800 mg) and ethyl acetate (100 cc) are added. After evaporation of the solvents, the residue is taken up in methylene chloride. After filtration over silica gel, 2,5,7,8-tetramethyl-2-(4′,8′,12′-trichloro-4′,8′,12′-trimethyl-tridecyl)-chroman-6-ol acetate (4.99 g) is obtained.

The degree of conversion of the 2,5,7,8-tetramethyl-2-(4′,8′,12′-trichloro-4′,8′,12′-trimethyl-tridecyl)-chroman-6-ol is 100%. The yield is 92.5%.

EXAMPLE 5

Zinc chloride (186 mg) and acetic acid (3 cc) are introduced, under an argon atmosphere, into a reactor. Trimethylhydroquinone (1.85 g), acetic acid (1.5 cc) and methylene chloride (4.5 cc) are then added. Thereafter, 1,7,11,15-tetrachloro-3,7,11,15-tetramethyl-hexadec-2-ene (5.1 g) dissolved in acetic acid (4 cc) and methylene chloride (4 cc) is added over the course of 15 minutes at 23° C. After 2 hours' stirring at a temperature of between 22° and 25° C., acetic anhydride (3.5 cc) is added. The temperature rises to 32° C. After 15 hours at a temperature of about 25° C., water (100 cc) is added, followed by sodium bicarbonate until the mixture is neutral. The mixture is extracted with ethyl acetate (twice 50 cc). The organic phases are dried over potassium carbonate. After filtration and evaporation of the solvent, an oil (5.82 g) containing 64% of 2,5,7,8-tetramethyl-2-(4′,8′,12′-trichloro-4′,8′,12′-trimethyl-tridecyl)-chroman-6-ol acetate is obtained.

The yield is 53%.

EXAMPLE 6

The product (1 g) obtained in Example 3, acetic acid (20 cc) and palladium on charcoal (0.1 g) containing 10% of palladium are introduced into a three-neck flask equipped with a magnetic stirrer, a thermometer and a condenser topped by a hydrogenation head. The reaction mixture is heated to 80° C. under hydrogen at atmospheric pressure. The theoretical amount of hydrogen is absorbed in 2 hours. After cooling, the catalyst is filtered off. After evaporation of the solvent, a very pale yellow oil (0.9 g) containing 89.5% by weight of tocopherol acetate is obtained.

EXAMPLE 7

The product (2.04 g) obtained in Example 1, palladium on charcoal (44 mg) containing 10% of palladium and ethanol (25 cc) are introduced into an autoclave. A hydrogen pressure of 50 bars is set up and the mixture is then heated at 80° C. for 5 hours, with constant agitation. After cooling, removal of the catalyst by filtration and evaporation of the solvent, tocopherol is obtained in a yield of 96%.

EXAMPLE 8

Anhydrous zinc chloride (990 mg=0.007 mole) dissolved in acetic acid (20 cc) is introduced, under an argon atmosphere, into a 250 cc three-neck flask. Trimethylhydroquinone (4.4 g=0.0289 mole) is then added. Onto this heterogeneous mixture is poured, over the course of 40 minutes at a temperature of between 20° and 26° C., a mixture (10 g) of 1,7-dichloro-3,7,11,15-tetramethyl-hexadec-2-ene and 3,7-dichloro-3,7,11,15-tetramethyl-hexadec-1-ene dissolved in acetic acid (20 cc). The mixture becomes homogeneous and has a brownish red colour. After 1 hour's stirring, acetic anhydride (10 cc) is added and stirring is then continued for a further 2 hours. After hydrolysis with water, extraction with ether and drying over magnesium sulphate, the solvent is evaporated under reduced pressure. This gives a yellow oil (16.2 g), analysis of which by mass spectrometry, proton nuclear magnetic resonance and $^{13}$C nuclear magnetic resonance shows that it consists essentially of 2,5,7,8-tetramethyl-2-(4'-chloro-4',8',12'-trimethyl-tridecyl)-chroman-6-ol acetate.

The degree of conversion (determined by measuring the recovered trimethylhydroquinone diacetate) is 80.4%.

The mixture of 1,7-dichloro-3,7,11,15-tetramethyl-hexadec-2ene and 3,7-dichloro-3,7,11,15-tetramethyl-hexadec-1-ene can be prepared in the following manner:

Triethylamine hydrochloride (360.5 mg=0.26×10$^{-2}$ mole), cuprous chloride (126 mg=0.13×10$^{-2}$ mole), acetic acid (9 cc) and methylene chloride (9 cc) are introduced, under an argon atmosphere, into a 250 cc flask. The mixture is stirred until a homogeneous yellow solution is obtained. This is cooled to 0° C. and 3-methylene-7,11,15-trimethylhexadeca-1,6-diene (13.96 g), of 95% purity, is then added rapidly. The solution is cooled to a temperature of about −5° C. and a stream of anhydrous hydrogen chloride gas is then passed through it for 1 hour 20 minutes so as to introduce hydrogen chloride (5 g=0.137 mole). After 30 minutes' stirring at a temperature of about −5° C., the reaction mixture is poured into pentane (20 cc) and an aqueous 10% strength by weight ammonium chloride solution (20 cc) at a temperature of about 20° C. The organic phase is separated off by decanting and then dried over sodium sulphate. After filtration and evaporation of the solvent, a crude product (17.31 g) is obtained, the analysis of which by mass spectrography and proton nuclear magnetic resonance shows the presence of 90% of a mixture of 1,7-dichloro-3,7,11,15-tetramethyl-hexadec-2-ene and 3,7-dichloro-3,7,11,15-tetramethyl-hexadec-1-ene.

To confirm the linearly of the skeleton of the product obtained, the product (1.7 g) obtained above, dissolved in ethanol (20 cc) is treated with hydrogen under a pressure of 20 bars at 80° C. in the presence of 10% strength palladium on charcoal (170 mg). After having filtered off the catalyst and evaporated the solvent, vapour phase chromatographic determination with an internal standard shows that the yield of phytane is 83.7% relative to the triene employed.

The selectivity in respect of phytane relative to the other isomers is 98%.

EXAMPLE 9

The procedure followed is an in Example 8, but starting from the following products:
a mixture of 1,7,15-trichloro-3,7,11,15-tetramethyl-hexadec-2-ene and 3,7,15-trichloro-3,7,11,15-tetramethyl-hexadec-1-ene: 10 g
trimethylhydroquinone: 4 g
zinc chloride: 914 mg
acetic acid: 43 cc
acetic anhydride: 10 cc After treatment of the reaction mixture, an orange oil (16.63 g) is obtained.

The degree of conversion of the trimethylhydroquinone is 81.3% (as determined by measuring the trimethylhydroquinone diacetate).

The structure of 2,5,7,8-tetramethyl-2-(4',12'-dichloro-4',8',12'-trimethyl-tridecyl)-chroman-6-ol acetate is confirmed by the mass spectrum and the proton nuclear magnetic resonance and $^{13}$C nuclear magnetic resonance spectra, using a purified fraction of the oil obtained.

The mixture of 1,7,15-trichloro-3,7,11,15-tetramethyl-hexadec-2-ene and 3,7,15-trichloro-3,7,11,15-tetramethyl-hexadec-1-ene can be prepared as follows:

The procedure of Example 1 is employed, but starting from the following products:
2-methylene-7,11,15-trimethyl-hexadeca-1,6,14-triene: 14 g (5.1×10$^{-2}$ mole)
triethylamine hydrochloride: 370 g
cuprous chloride: 130 mg
acetic acid: 9 cc
methylene chloride: 9 cc A stream of anhydrous hydrogen chloride gas is passed through the mixture for 1 hour so as to introduce hydrogen chloride (7.3 g).

After treatment of the reaction mixture, an oil (19.31 g) is obtained, analysis of which by mass spectrometry and by proton nuclear magnetic resonance shows that it consists essentially of 1,7,15-trichloro-3,7,11,15-tetramethyl-hexadec-2-ene and 3,7,15-trichloro-3,7,11,15-tetramethyl-hexadec-1ene and that it does not contain conjugated dienes.

The hydrogenation of the product obtained under the conditions described in Example 1 shows that according to vapour phase chromatographic determination using an internal standard, the yield of phytane is 63% relative to the 2-methylene-7,11,15-trimethyl-hexadeca-1,6,14-triene employed.

EXAMPLE 10

The product (6.67 g) obtained in Example 8, acetic acid (60 cc) and palladium on charcoal (400 mg) containing 10% by weight of palladium are introduced into a hydrogenation apparatus. The mixture is heated at 80° C. for 2 hours 30 minutes under a hydrogen pressure of 1 bar. After cooling, filtering off the catalyst and evaporating the solvent, a clear oil (5.62 g) contaning 74.7% of tocopherol acetate is obtained.

The yield of tocopherol acetate is 93% relative to the trimethylhydroquinone converted, and 80% relative to the 3-methylene-7,11,15-trimethyl-hexadeca-1,6-diene converted.

The degree of conversion of the 1,7-dichloro-3,7,11,15-tetramethyl-hexadec-2-ene and 3,7-dichloro-3,7,11,15-tetramethyl-hexadec-1-ene is 97%, the determination being carried out by measuring the phytane recovered.

EXAMPLE 11

The oil (2.9 g) obtained in Example 9 is dissolved in acetic acid (30 cc) containing palladium on charcoal (220 mg) itself containing 10% by weight of palladium. The mixture is heated at 80° C. for 4 hours 30 minutes under a hydrogen pressure of 1 bar. After treatment of the reaction mixture, a clear oil (2.17 g) containing tocopherol acetate (62%) is obtained.

The yield of tocopherol acetate is 76.7% relative to the trimethylhydroquinone converted and 65% relative to the 2-methylene-7,11,15-trimethyl-hexadeca-1,6,14-triene converted.

The degree of conversion of the 1,7,15-trichloro-3,7,11,15-tetramethyl-hexadec-2-ene and 3,7,15-trichloro-3,7,11,15-tetramethyl-hexadec-1-ene is 97%, the determination being carried out by measuring the phytane recovered.

We claim:
1. A tocopherol derivative of the formula:

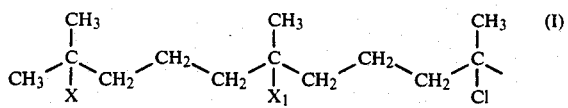

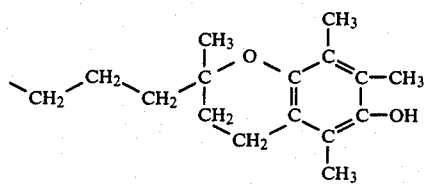

in which X and $X_1$, which may be identical or different, each represent hydrogen or chlorine, or the acetate thereof.

2. A compound according to claim 1 which is 2,5,7,8-tetramethyl-2-(4',8',12'-trichloro-4',8',12'-trimethyl-tridecyl)-chroman-6-ol.

3. A compound according to claim 1 which is 2,5,7,8-tetramethyl-2-(4',8',12'-trichloro-4',8',12'-trimethyl tridecyl)-chroman-6-ol acetate.

4. A compound according to claim 1 which is 2,5,7,8-tetramethyl-2-(4'-chloro-4',8',12'-trimethyl-tridecyl)-chroman-6-ol acetate.

5. A compound according to claim 1 which is 2,5,7,8-tetramethyl-2-(4',12'-dichloro-4',8',12'-trimethyl-tridecyl)-chroman-6ol acetate.

* * * * *